USOO5454773A

United States Patent [19]
Blanchard et al.

[11] Patent Number: 5,454,773
[45] Date of Patent: Oct. 3, 1995

[54] MUSCLE EXERCISE AND REHABILITATION APPARATUS

[75] Inventors: Frederick W. Blanchard, Hixson, Tenn.; Roy G. Browder, Henegar, Ala.

[73] Assignee: Chattanooga Group, Inc., Hixson, Tenn.

[21] Appl. No.: 72,337

[22] Filed: Jun. 4, 1993

[51] Int. Cl.[6] .................................................. A63B 21/00
[52] U.S. Cl. .......................... 482/133; 482/136; 482/142; 482/901; 482/908; 601/24; 601/33
[58] Field of Search .................................. 482/4, 52, 55, 482/57, 70, 71, 72, 100, 133, 134–137, 142, 901, 908; 601/24, 26, 33; 73/379.06, 379.08, 379.09; 297/122

[56] References Cited

U.S. PATENT DOCUMENTS

| | | | |
|---|---|---|---|
| 3,053,568 | 9/1962 | Miller | 601/24 |
| 3,323,366 | 6/1967 | De Lorme, Jr. et al. | 601/26 |
| 4,333,340 | 6/1982 | Elmeskog | |
| 4,711,450 | 12/1987 | McArthur | |
| 4,772,015 | 9/1988 | Carlson et al. | 482/908 |
| 4,905,676 | 3/1990 | Bond et al. | |
| 5,054,774 | 10/1991 | Belsito | |
| 5,163,451 | 11/1992 | Grellas | 601/33 |
| 5,209,223 | 5/1993 | McGorry et al. | |

FOREIGN PATENT DOCUMENTS 0251656  6/1987  European Pat. Off.

OTHER PUBLICATIONS

Chattanooga Group, Inc., "Kin–Com 125E Plus", 1992, 2 Page Brochure.

Circle Reader Service No. 127, "MERAC" by Universal, 1 Page Brochure.

*Primary Examiner*—Stephen R. Crow
*Assistant Examiner*—Jeanne M. Clark
*Attorney, Agent, or Firm*—Bell, Seltzer, Park & Gibson

[57] ABSTRACT

An improved muscle exercise and rehabilitation apparatus, which includes a rotary actuator mounted for linear movement along a longitudinal path of movement, and a seat assembly which is mounted for movement along a lateral path of movement, and with the longitudinal path disposed on one side of the lateral path and having one end which intersects the lateral path at a medial location along the length of the lateral path. Also, the rotary actuator is mounted so as to be laterally offset from its supporting post so as to permit the actuator to rotate a full 360° about a vertical axis, and a full 360° about a horizontal axis. The resulting flexibility in the orientation and positioning of the components of the apparatus permits the apparatus to be readily configured to perform a variety of exercising routines, including gravity eliminated exercises. A novel automatic positioning system for the seat assembly and actuator is disclosed, and a novel patient stabilizing system is also disclosed.

19 Claims, 13 Drawing Sheets

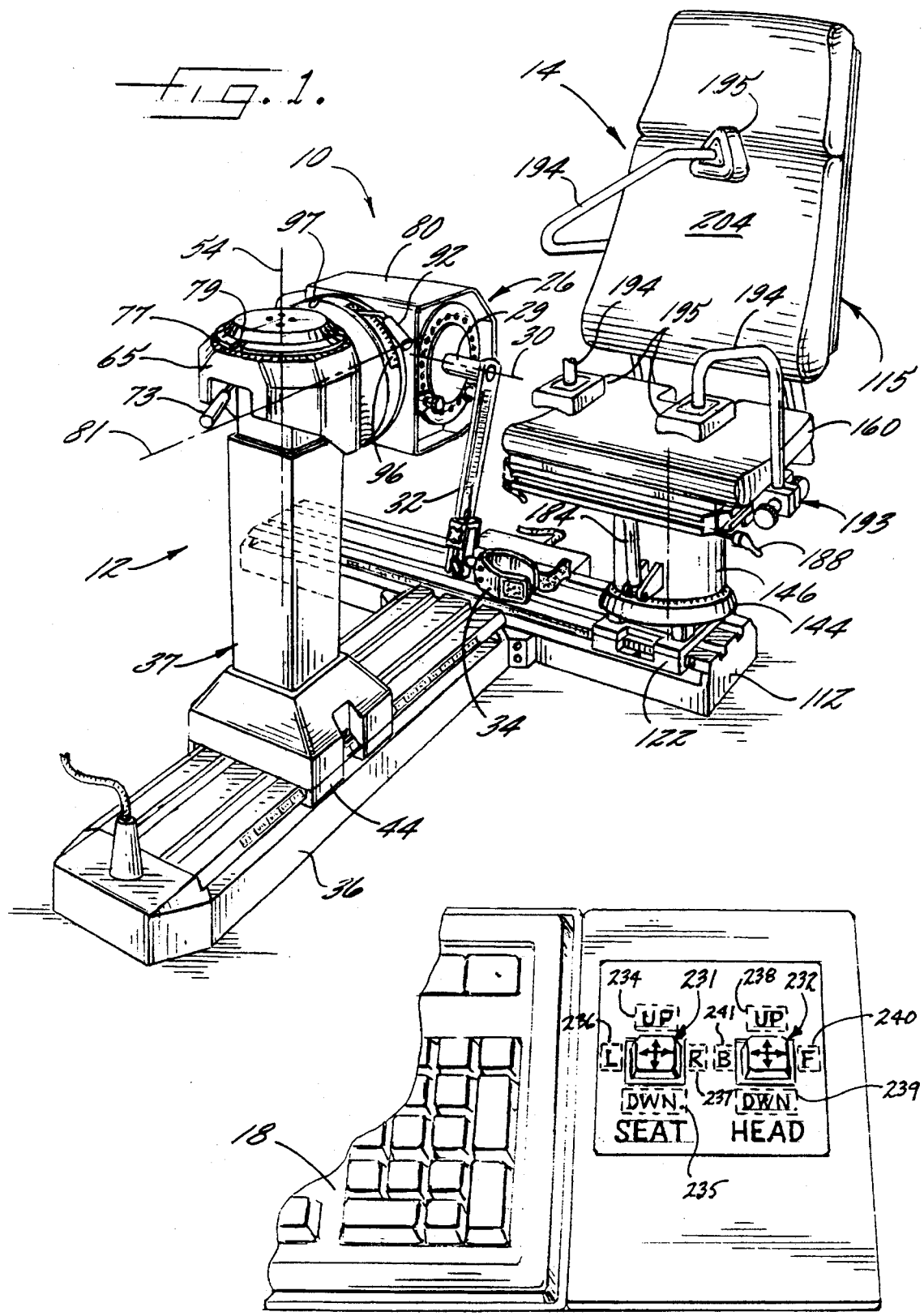

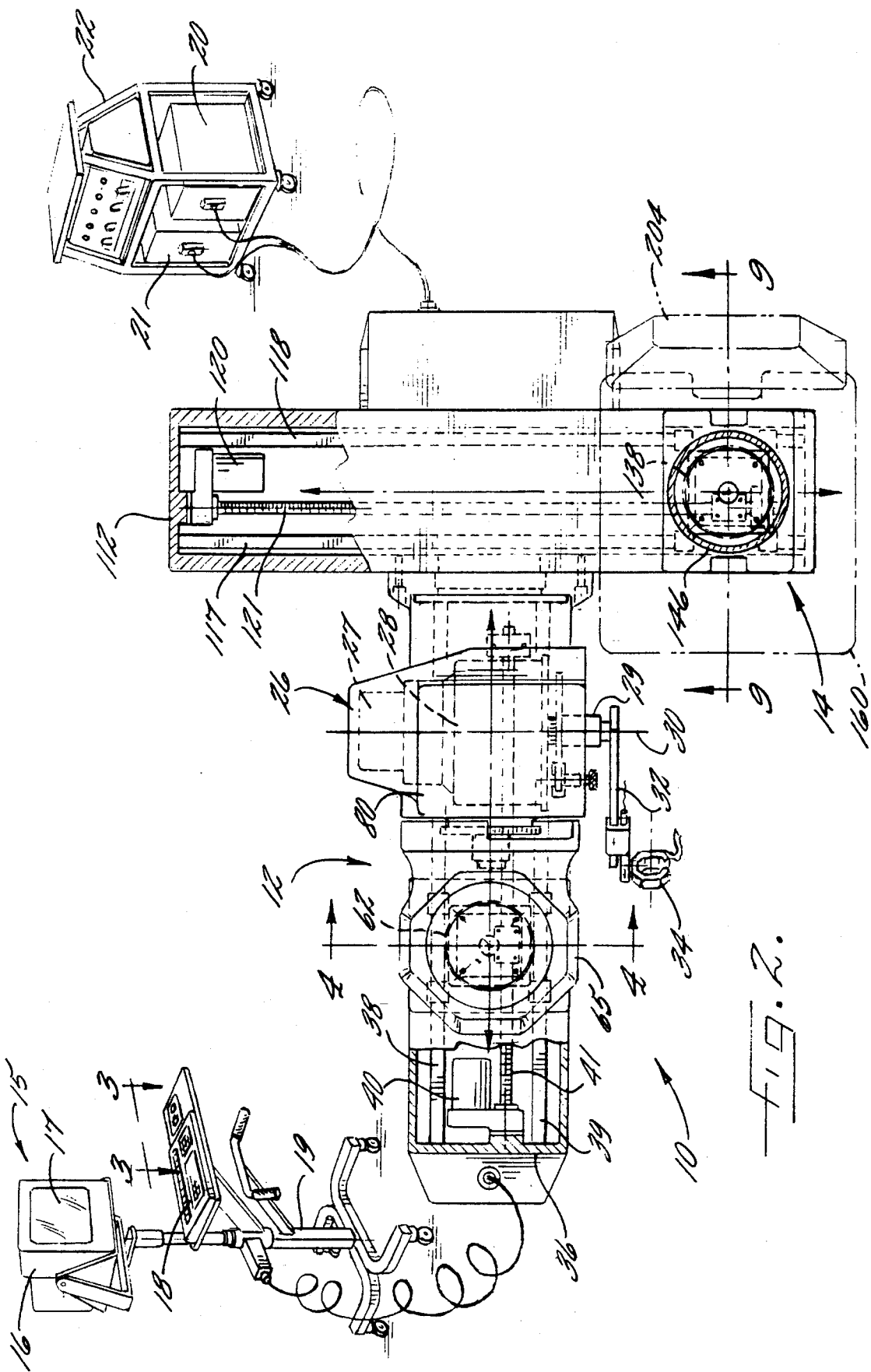

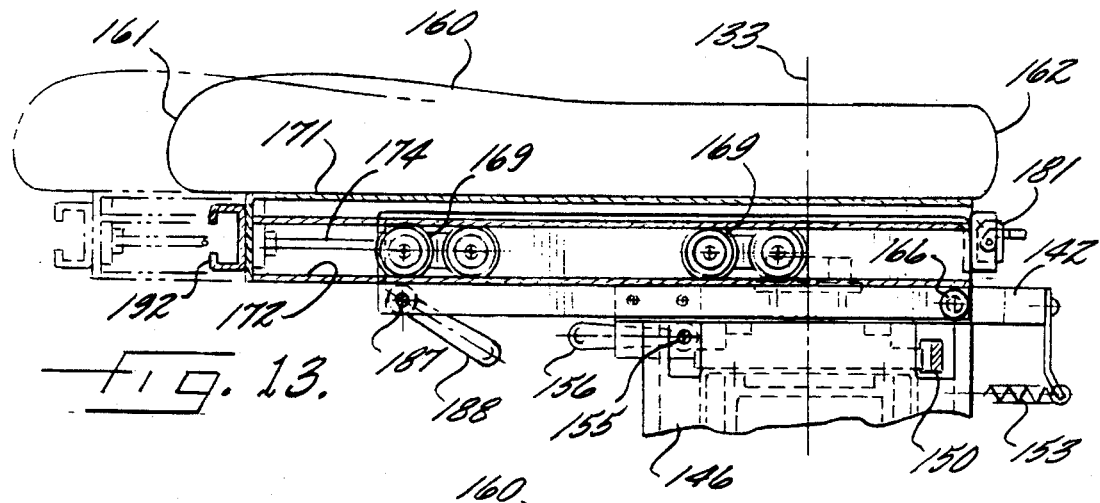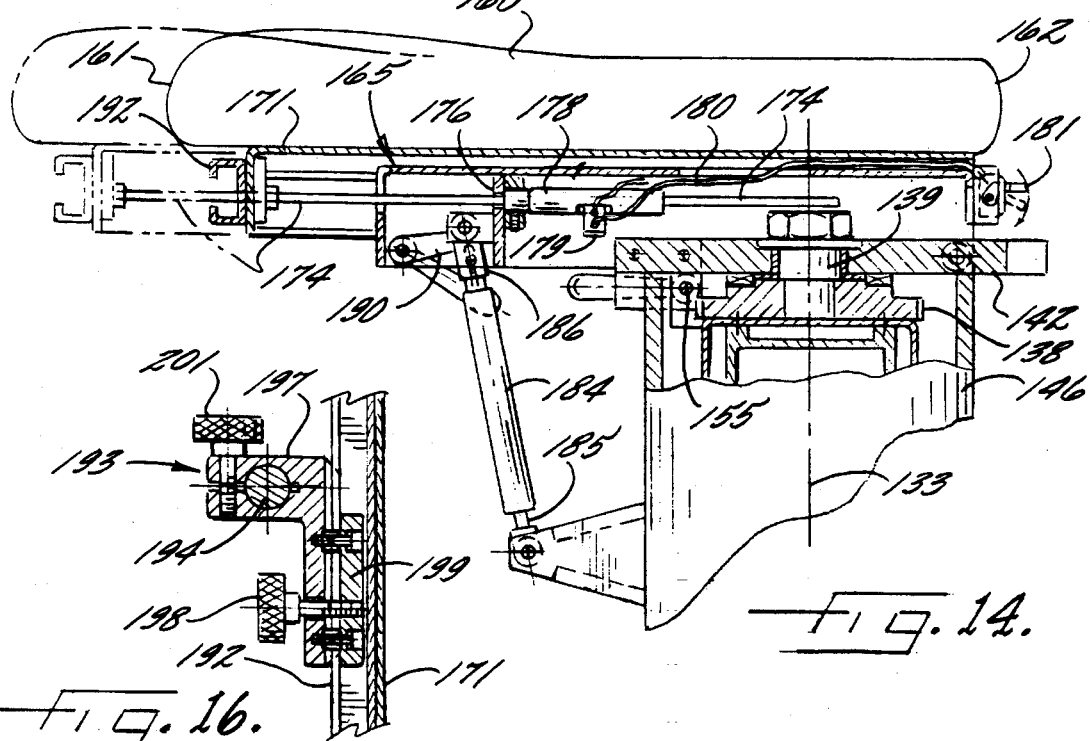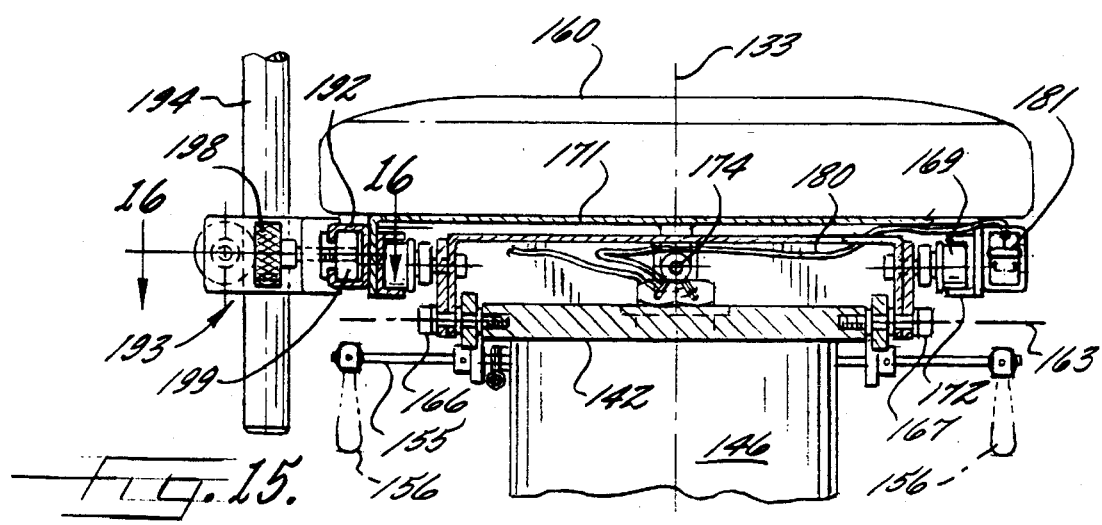

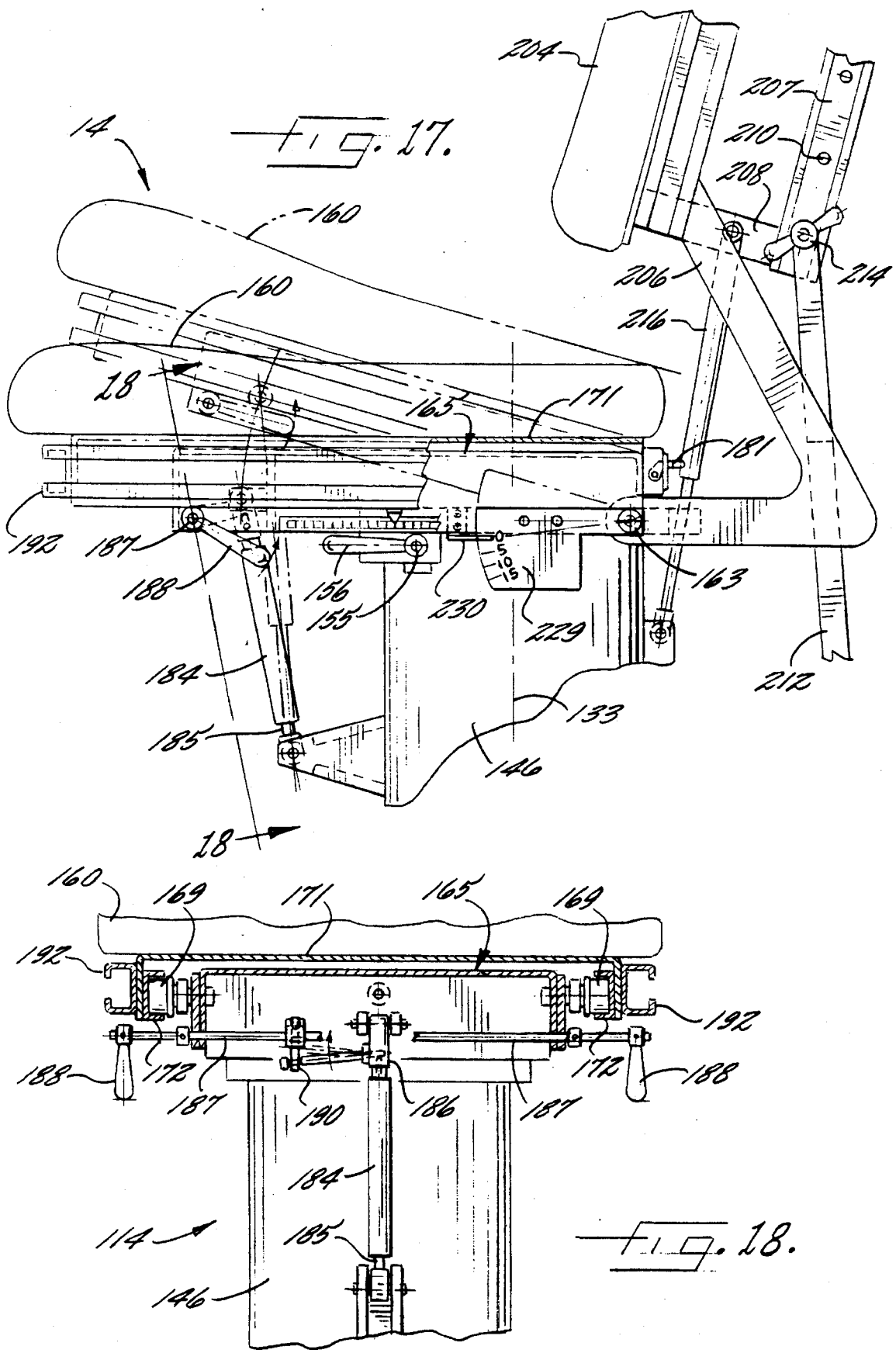

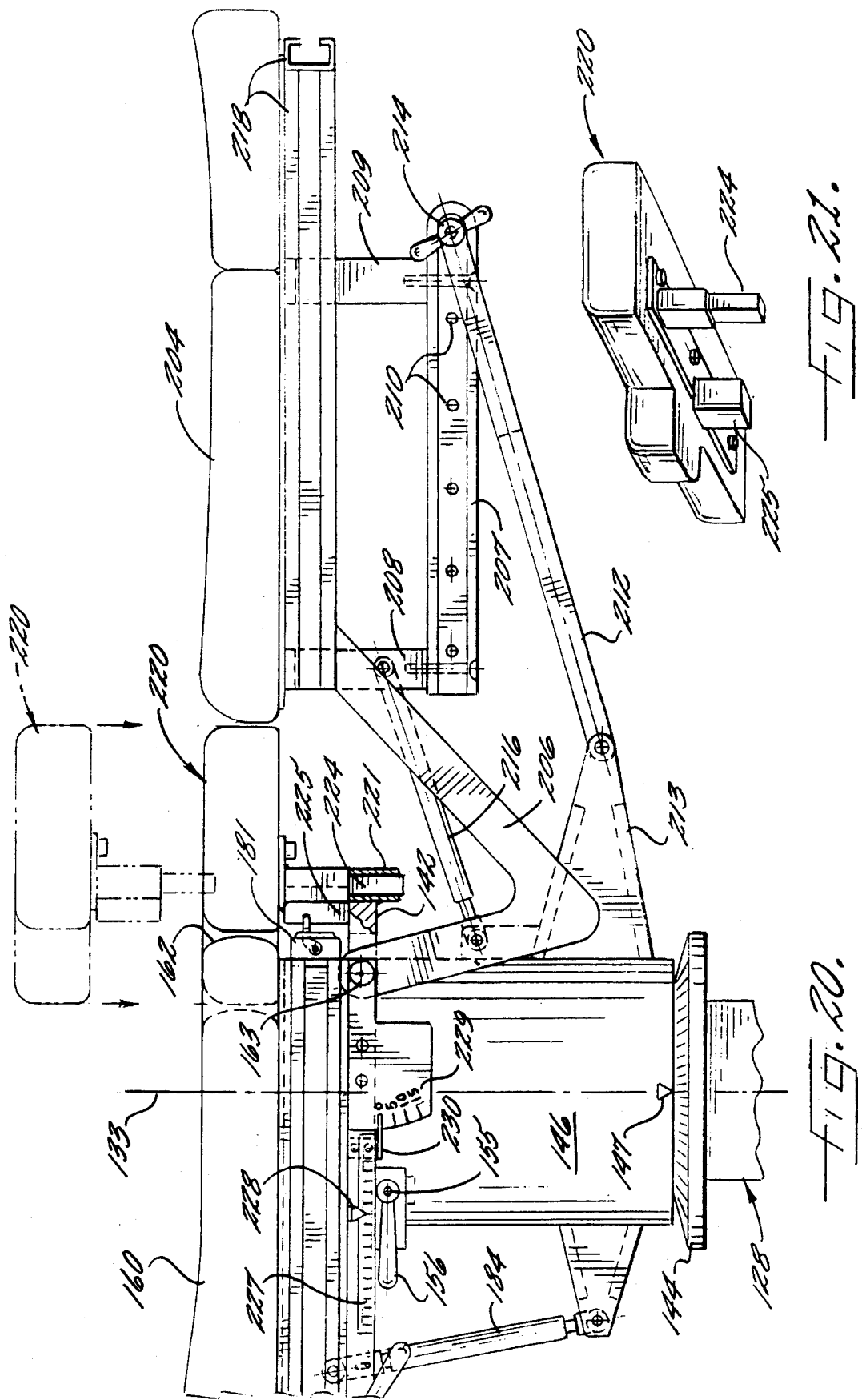

MUSCLE EXERCISE AND REHABILITATION APPARATUS

BACKGROUND OF THE INVENTION

The present invention relates to a computer controlled apparatus adapted for analysis, assessment, and evaluation of musculoskeletal performance.

U.S. Pat. No. 4,711,450 to McArthur discloses a computer controlled apparatus of the described type, and which comprises a powered rotary actuator which is mounted on a pedestal located between two seats. The apparatus as disclosed in the referenced patent has been sold for several years under the trademark KIN-COM® by Chattanooga Group Inc. of Chattanooga, Tenn., and the apparatus is adapted to operate in a number of different exercising modes, including isokinetic, isometric, isotonic, and constant power modes.

The actuator of the KIN-COM® apparatus may be elevated to a desired elevation suited for a particular patient and a particular exercising mode, and the actuator may also be rotated about a horizontal axis which extends between the two seats. In use, the patient sits or lies on one of the two seats, and the elevation and rotational orientations of the actuator are adjusted to fit the requirements of the selected exercising mode to the particular patient. In this regard, it is preferable that the rotational axis of the actuator be aligned to extend through the joint of the patient which is being exercised or evaluated.

In another prior version of the KIN-COM® apparatus, which is known as the "125 E" model, the apparatus comprises a single seat, and the powered rotary actuator is mounted on a support column which is pivotable about a vertical axis which extends through the seat, and so as to permit the actuator to be selectively positioned on either side or in front of the seat. Also, in the "125 E" model, the actuator is vertically movable under a powered control system, and the actuator pivots with respect to its support column about a vertical axis, and it also tilts with respect to its support column about a horizontal axis. Further, the seat is adjustable in several respects, and it comprises a seat portion and a back rest which is pivotable between upright and horizontal positions, and the seat portion and back rest are adjustable together in the longitudinal direction, and they pivot together about a vertical axis. Further, the seat portion is adjustable independently of the back rest in the longitudinal direction, and the supporting structure for the seat portion and back rest is movable vertically by a power control system.

It is an object of the present invention to provide an improved exercising and evaluation apparatus of the described type, and which has an improved and simplified set-up capability wherein the machine may be readily configured to perform a selected exercising routine for a particular patient.

It is also an object of the present invention to provide an exercising and evaluation apparatus having improved flexibility in the operational configurations of the apparatus, and so as to permit an increased variety of exercising modes, including gravity eliminated exercises.

It is a further object of the present invention to provide an exercising and evaluation apparatus of the described type which has improved provision for stabilizing the patient on the seat of the apparatus.

It is a more particular object of the present invention to provide an exercising and evaluation apparatus of the described type which has an automatic positioning system whereby the seat and actuator of the apparatus may be automatically located for a particular exercising mode for a particular patient.

SUMMARY OF THE INVENTION

The above and other objects and advantages of the present invention are achieved in the embodiment illustrated and described herein by the provision of a muscle exercise and rehabilitation apparatus which comprises a rotary actuator comprising an output shaft defining a rotational axis, an arm connected to the output shaft and extending radially therefrom and so as to be adapted for engagement by a patient, and drive means for selectively rotating the shaft in either direction about the rotational axis. The actuator is mounted by mounting means which comprises a vertically disposed post which defines a vertical axis, a first housing member mounted to the post for rotation about the vertical axis, and a second housing member mounted to the first housing member for rotation about a horizontal axis which is fixed with respect to the first housing member, and with the actuator being mounted to the second housing member with the rotational axis of the output shaft being disposed in a vertical plane which is perpendicular to the horizontal axis and offset from the vertical axis of the post in the direction of the horizontal axis, and such that the actuator can be rotated through a rotational range of movement about the horizontal axis so as to permit the rotational axis of the output shaft selectively to be disposed vertically in either direction and horizontally in either direction.

The actuator mounting means preferably comprises a base member supporting the post, and a first drive motor for vertically moving the first and second housing members and the actuator collectively with respect to the base member. Further, the post may be moved horizontally along the base member in either direction along a longitudinal path of movement, and a second drive motor is provided in the base member for effecting such movement in either direction.

The apparatus of the invention also preferably includes a seat assembly for supporting a patient thereon and so that the patient can engage the arm of the actuator. The seat assembly is mounted by means of a base member, and a post which is mounted to the base member for movement along a laterally directed path of movement which is perpendicular to the longitudinal path of movement of the rotary actuator, with the seat assembly being mounted to the upper end of the post. In addition, the longitudinal path of movement of the rotary actuator is perpendicular to and on one side of the lateral path of movement of the seat assembly, and the longitudinal path of movement has one end disposed immediately adjacent the lateral path of movement at a medial location along the length of the lateral path of movement. The mounting means for the seat assembly also includes a first drive motor mounted in the base member for moving the post along the laterally directed path of movement, and a second drive motor mounted in the post for raising and lowering the seat assembly.

The seat assembly preferably comprises a seat portion and a back rest, and the seat portion is mounted for forward and back adjustment independent of the back rest, and tilting movement wherein the forward edge of the seat portion may be raised. Also, the back rest is mounted for pivotal movement between an upright position and a lowered position where it is substantially co-planar with the seat portion.

The apparatus of the present invention also preferably includes an automatic positioning system, wherein the actuator and the seat assembly can be readily positioned at the optimum settings for a particular exercising routine and for a particular patient.

BRIEF DESCRIPTION OF THE DRAWINGS

Some of the objects and advantages of the present invention having been stated, others will appear as the description proceeds, when taken in conjunction with the accompanying drawings, in which;

FIG. 1 is a perspective view showing a computer controlled exercising machine which embodies the features of the present invention;

FIG. 2 is a partly sectioned and partly schematic top plan view of the apparatus;

FIG. 3 is a fragmentary view of the keyboard of the apparatus taken substantially along the line 3—3 of FIG. 2, and illustrating the control switches associated with the patient positioning system of the present invention;

FIG. 13 is a fragmentary and sectioned side elevation view of the seat assembly taken substantially along the line 13—13 of FIG. 10;

FIG. 14 is a view similar to FIG. 13 but taken substantially along the line 14—14 of FIG. 10;

FIG. 15 is a sectioned side elevation view taken substantially along the line 15—15 of FIG. 10;

FIG. 16 is a fragmentary and sectioned view of a mounting car and taken substantially along the line 16—16 of FIG. 15;

FIG. 17 is a fragmentary and partly sectioned side elevation view of the seat assembly and illustrating the seat portion in its lowered position in solid lines and in its upwardly tilted position in dashed lines;

FIG. 18 is a fragmentary and partly sectioned front elevation view of the seat assembly and taken substantially along the line 18—18 of FIG. 17;

FIG. 19 is a rear elevation view of the seat assembly;

FIG. 20 is side elevation view of the seat assembly with the back rest in its horizontal position, and further illustrating the intermediate pad;

FIG. 21 is a perspective view of the intermediate pad of the seat assembly;

DETAILED DESCRIPTION OF THE PREFERRED EMBODIMENT

Figure 4:
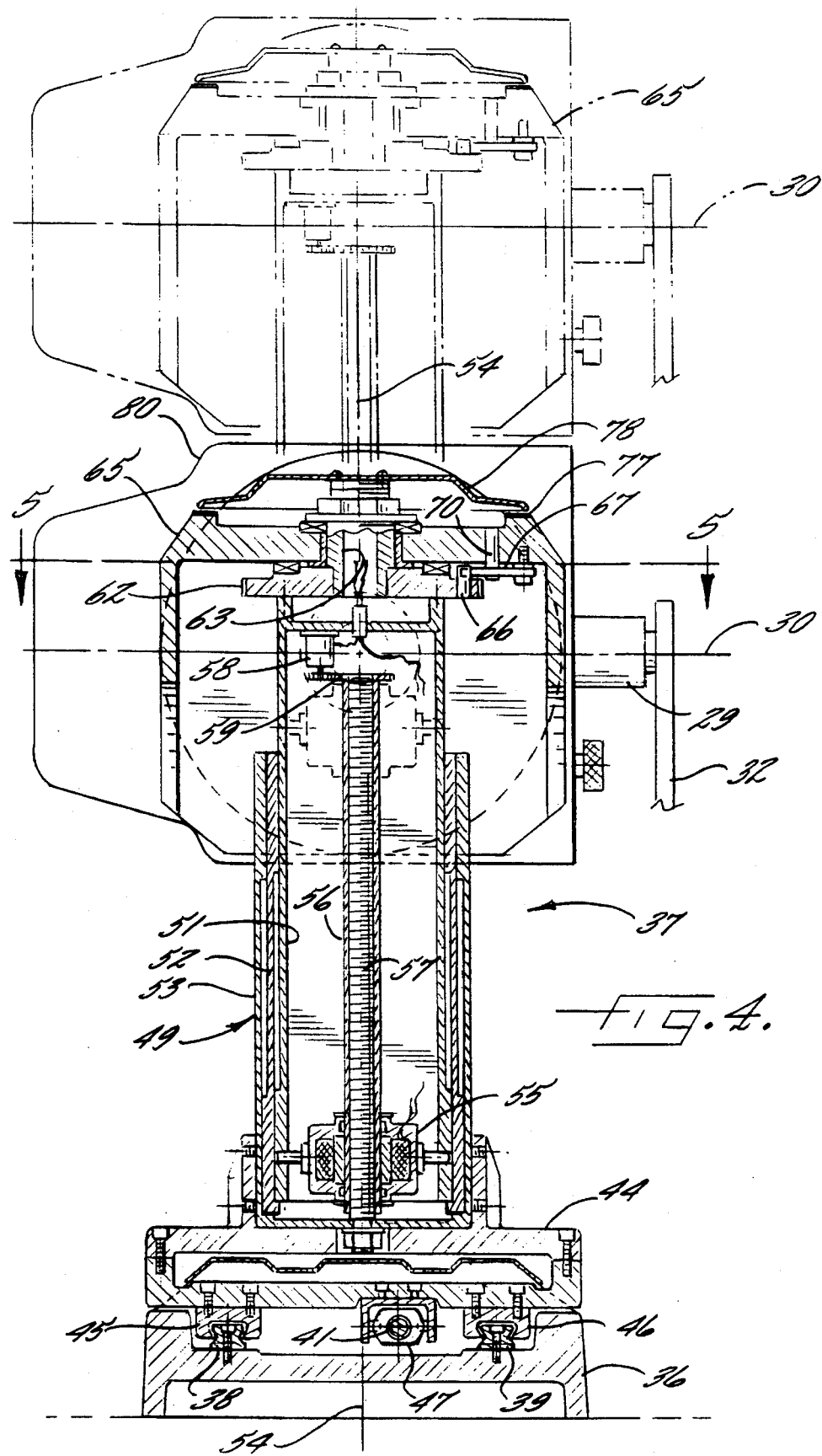
FIG. 4 is a sectioned side elevation view of the actuator assembly of the apparatus and taken substantially along the line 4—4 of FIG. 2.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, the illustrated embodiment is provided so that this disclosure will be thorough and complete, and will fully convey the scope of the invention to those skilled in the art. Like numbers refer to like elements throughout.

Overview Of The Apparatus

Referring to FIGS. 1 and 2, a computer controlled exercising machine which embodies the features of the present invention is illustrated generally at 10. The apparatus 10 consists of an actuator assembly 12 and an adjacent patient support assembly 14. The positioning of the actuator assembly and patient support assembly, as well as the mechanical operation of the apparatus, is controlled by a computer controller 15, which in turn comprises a monitor 16 including a display screen 17, and a keyboard 18, which are mounted on a portable stand 19. The controller 15 also includes a control processing unit 20 and associated box assembly 21 which are mounted on another portable stand 22. A computer controller of this type is further described in U.S. Pat. No. 5,054,774 to Belsito, the disclosure of which is expressly incorporated herein by reference.

The Actuator Assembly

The actuator assembly 12 of the apparatus 10 is best seen in FIGS. 1, 2, and 4–8, and it includes a rotary actuator 26 which preferably comprises a DC reversible and variable speed electric servo motor 27 having a power rating of about 1 ½ horsepower. The motor 27 has an output which acts through a 100:1 gear box 28, to turn an output shaft 29 which is mounted for rotation about a rotational axis 30. A radial arm 32, which typically has a length of about 17 inches, is connected to the output shaft 29, and the arm 32 in turn releasably mounts a patient engaging member 34 which is adapted for the particular exercising mode to be performed with the patient. The patient engaging member 34 is releasably and slidably mounted to the arm 32 so as to permit members of different configuration, designed for a variety of exercising routines, to be selectively attached to the arm. In addition, the member 34 includes a load cell (not shown) for measuring the force applied thereto by the patient, and for the purposes more fully described in U.S. Pat. No. 4,711,450 to McArthur, the disclosure of which is expressly incorporated herein by reference.

The rotary actuator 26 is mounted by a structure which includes an actuator base member 36 having a vertical post 37 slidably mounted thereto. More particularly, the base member 36 is adapted to be positioned on the supporting floor, and it includes a pair of longitudinally extending slides 38, 39. Also, an AC reversible electric motor 40 is mounted in the base member, and the output of the motor is connected to a longitudinally extending threaded drive screw 41 which is disposed between the slides.

The vertical post 37 is slidably mounted to the base member 36, and the post 37 includes a lower frame 44 which includes a pair of downwardly open C-shaped grippers 45, 46 for engaging the two slides 38, 39 respectively. Also, the lower frame 44 mounts a nut 47 which threadedly engages the drive screw 41, so that rotation of the drive motor 40 and the screw 41 causes the post 37 to slide back and forth along a longitudinal path of movement defined by the slides 38, 39. The output of the motor 40 is connected to a conventional potentiometer (not shown) which signals the rotational position of the motor and thus the longitudinal position of the post 37 to the computer controller 15.

The post 37 further includes a telescopic pillar 49 which is fixed to the lower frame 44. As best seen in FIG. 4, the telescopic pillar 49 includes three concentric tubular members 51, 52, 53 of rectangular outline in transverse cross-section, and which are disposed coaxially about a vertical axis 54. An AC reversible electric drive motor 55 is fixed in the interior tubular member 51, and the output of the drive motor 55 is connected to a sleeve 56 which is coaxial with the vertical axis 54, and which is threaded onto a vertical threaded rod 57 which is also coaxial with the vertical axis 54 and is fixed to the lower frame 44.

Rotation of the drive motor 55 thus causes the sleeve 56 to rotate upon the threaded rod 57, which in turn causes the interior tubular member 51 to lift upwardly or return downwardly. Upon lifting a predetermined distance, the interior tubular member 51 engages the intermediate member 52, so as to lift the intermediate member, and likewise, the intermediate member 52 later engages the outer member 53 to define the limit of upper movement.

The telescopic pillar 49 as described above is itself of conventional design, and a pillar of the described configuration is manufactured by Magnetic Elektromotoran AG of Liestal, Germany. In the present apparatus, however, a potentiometer 58 is added, which is mounted in the pillar 49 so as to engage a gear wheel 59 which is coaxially mounted at the upper end of the sleeve 56, so that the rotational movement, and thus the elevation of the pillar may be determined and signalled to the computer controller.

The upper end of the interior member 51 is closed, and a circular external gear 62 is coaxially fixed thereto. A tubular shaft 63 is coaxially mounted to the gear 62, and the shaft 63 rotatably mounts a first housing member 65, such that the first housing member is free to rotate with respect to the post 37 about the vertical axis 54.

Figure 5:
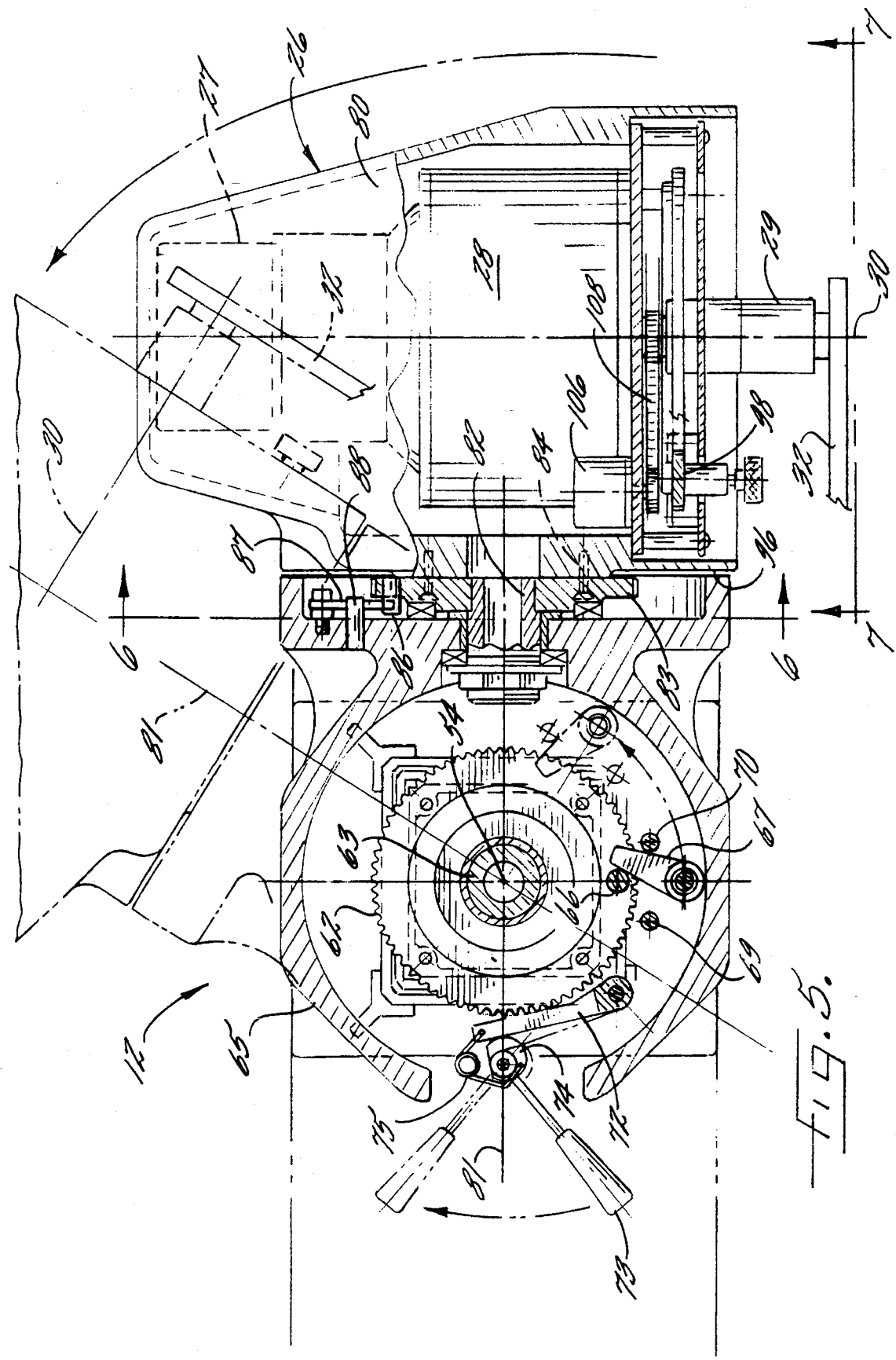
FIG. 5 is a sectioned plan view of the actuator assembly taken substantially along the line 5—5 of FIG. 4.

As best seen in FIG. 5, an abutment assembly is mounted to the post 37 and the first housing member 65 for precluding rotational movement of the first housing member 65 about the vertical axis 54 beyond a range which is somewhat greater than 360°. This abutment assembly includes an upright pin 66 fixed to the gear 62, and a lever arm 67 pivotally mounted to the first housing member for rotation about a vertical axis which is spaced from but parallel to the axis 54. A pair of pins 69, 70 are mounted to the first housing member adjacent the opposite sides of the lever arm 67 so as to permit limited pivotal movement of the lever arm. As seen in solid lines in FIG. 5, the first housing member 65 is positioned at the limit of its clockwise rotational movement, and it is adapted to rotate counterclockwise until the lever arm 67 engages the opposite side of the pin 66, which in turn causes the lever arm 67 to pivot into engagement with the side pin 69, thereby precluding further rotation. By this arrangement, the first housing member is able to rotate through a range slightly greater than 360°, e.g. about 380°.

To temporarily lock the first housing member 65 in a selected position, there is provided a rack gear 72 which is pivotally mounted to the first housing member 65. The movement of the rack gear 72 is controlled by a lever arm 73, which is also pivotally mounted to the first housing member 65, and which mounts a cam 74 for engaging the rack gear 72. Thus, as illustrated in FIG. 5, movement of the lever arm 73 counterclockwise to its illustrated solid line position causes the rack gear 72 to engage the circular gear 62 and thus preclude rotation of the first housing member, whereas movement of the lever arm 73 in the clockwise direction to the dashed line position releases the rack gear 72. A spring 75 is provided to separate the rack gear 72 from the circular gear 62 in this position, and thus permit rotation of the first housing member 65 within the range as described above.

For the purpose of permitting a visual determination of the rotational position of the first housing member 65 about the vertical axis 54, the upper portion of the first housing member mounts a circular scale 77 which is coaxial with the vertical axis 54 (FIGS. 1 and 4), and the upper end of the tubular shaft 63 mounts a circular cover plate 78. The cover plate 78 includes a pointer in the form of a narrow slot 79 on its outer periphery, which permits the scale to be read by the operator.

The actuator mounting means further comprises a second housing member 80 which is mounted to the first housing member 65 for rotation about a horizontal axis 81 (FIGS. 1 and 5) which is fixed with respect to the first housing member 65. More particularly, and as best seen in FIG. 5, the horizontal axis 81 perpendicularly intersects the vertical axis 54 of the post. This mounting arrangement includes a tubular shaft 82 which is rotatably mounted to the first housing member 65 coaxially with respect to the horizontal axis 81, and the shaft 82 fixedly mounts a circular gear 83 thereto, which is also coaxial with the horizontal axis 81. The gear 83 in turn mounts the second housing member 80 by means of bolts 84.

Figure 6:
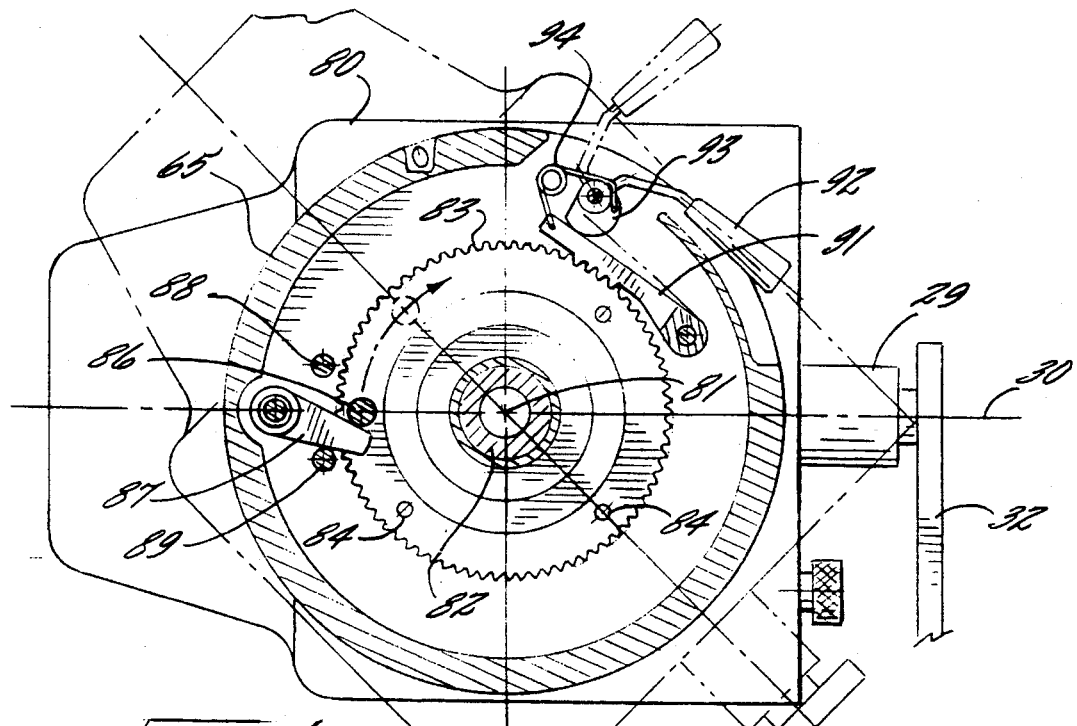
FIG. 6 is a sectioned side elevation view of the actuator assembly taken substantially along the line 6—6 of FIG. 5.
Figures 7, 8:
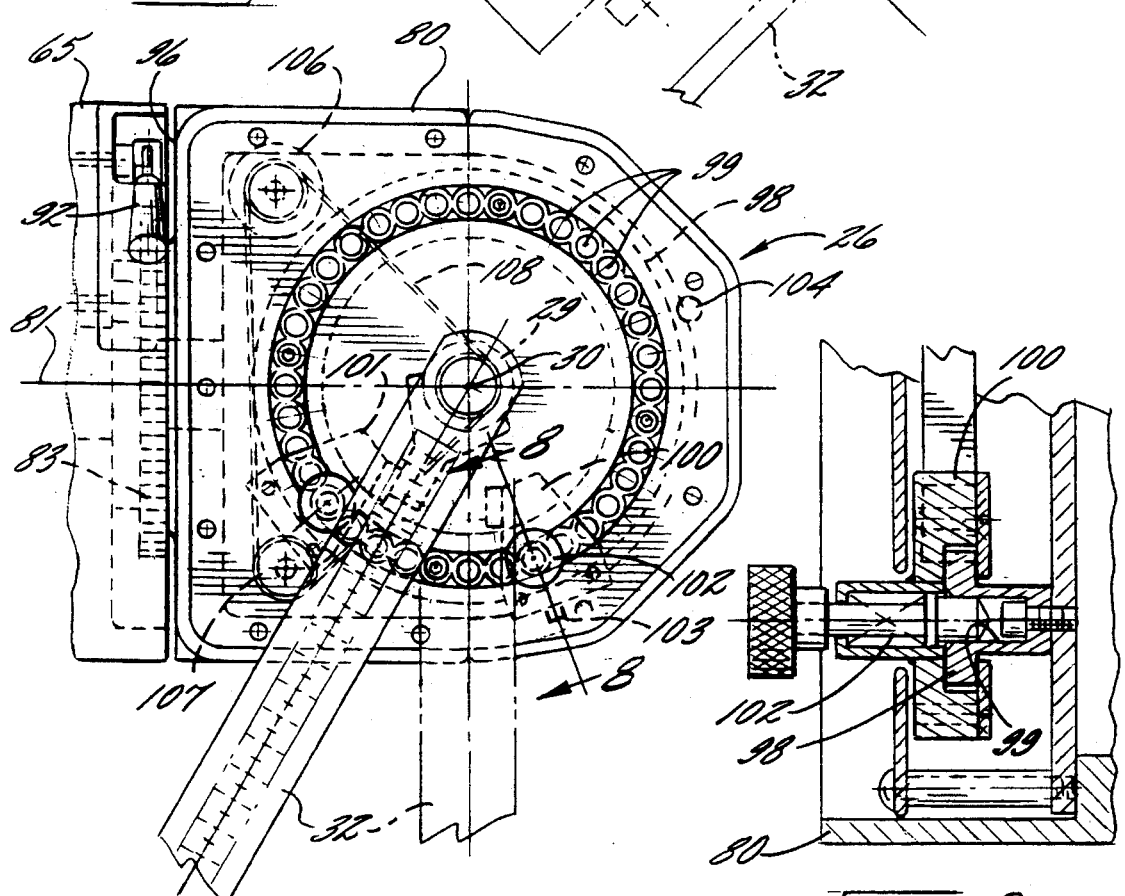
FIG. 7 is a side elevation view of the actuator assembly taken substantially along the line 7—7 of FIG. 5.
FIG. 8 is an enlarged sectional taken substantially along the line 8—8 of FIG. 7.

As best seen in FIGS. 5 and 6, the second housing member 80 includes an abutment assembly which is similar to that described above, and which is for the purpose of limiting the rotational range of the second housing member 80 about the horizontal axis 81. This abutment assembly comprises a pin 86 fixed to the gear, a lever arm 87 pivotally mounted to the first housing member 65, and a pair of side pins 88, 89 fixed to the first housing member 65. The operation of this abutment assembly is substantially identical to that described above, and it will accordingly be understood that the gear 83 and the second housing member 80 may be rotated clockwise through a range which is somewhat greater than 360° from the position illustrated in FIG. 6.

A rack gear 91, a lever arm 92, cam 93, and spring 94 are also mounted to the second housing member 80, so as to permit the second housing member to be temporarily locked with respect to the first housing member, in the manner described above with respect to the rack gear 72.

For the purpose of permitting a visual determination of the rotational position of the second housing member 80 about the horizontal axis 81, there is provided a circular scale 96 on the end surface of the second housing member 80, with the scale 96 being coaxial with the horizontal axis 81. The adjacent portion of the first housing member 65 includes a narrow slot 97, which permits the scale to be read by the operator.

The DC servo motor 27 and gear reducer 28 of the actuator are mounted within the second housing member 80, such that the rotational axis 30 of the output shaft 29 perpendicularly intersects the horizontal axis 81. Also, it will be seen that the rotational axis 30 is horizontally offset from the vertical axis 54 of the post 37 a distance sufficient to permit the second housing member 80 to freely rotate a full 360° about the horizontal axis 81. This offset distance is preferably at least about 15 inches, and as a result the rotational axis 30 can be disposed vertically in either direction, and horizontally in either direction.

The actuator assembly 12 further includes a limitation system for limiting the rotational movement of the output shaft 29, and thus the radial arm 32, about the rotational axis 30. This limitation system includes a ring-like plate 98 which is mounted to the second housing member 80 so as to coaxially surround the rotational axis 30, and the plate 98 includes a plurality of openings 99 spaced circumferentially thereabout. Also, two limit blocks 100, 101 are provided which are each slidably mounted to the plate 98 and adapted to be locked in a selected one of the openings by means of a releasable pin 102, with a right-hand one of the blocks 100 being configured to engage the arm 32 so as to limit its counterclockwise movement and with the other or left-hand block 101 being configured to engage the arm 32 so as to limit its clockwise movement.

The right-hand block 100 mounts a pin 103 which engages a stop 104 on the second housing member, to define the full counterclockwise position of the arm and a maximum range of about 270° when the left-hand block is mounted adjacent the right-hand block. To set the arm 32 for movement outside this range, the arm 32 is rotated clockwise to the end of the 270° range, and the right-hand block 100 is moved about the ring-like plate 98 until its pin 103 engages the other side of the stop 104. The actuator may then be operated at the other end of its full 360° range.

The second housing member 80 also mounts a tachometer 106 and a potentiometer 107, which are operatively connected to the output shaft via drive belt 108. The tachometer and potentiometer send signals representing the speed and rotational position of the output shaft, respectively, to the computer controller 15, for the purpose of controlling the operation of the apparatus in the manner more fully described in the above-cited prior patent to McArthur.

The Patient Support

The patient support assembly 14 of the apparatus 10 comprises a seat base member 112, a vertical post 114 slideably mounted to the base member 112, and a seat assembly 115 which is mounted to the upper end of the post 114. The base member 112 is adapted to rest upon the supporting floor and so as to define a lateral direction which is perpendicular to the longitudinal direction defined by the actuator base member 36.

The seat base member 112 includes a pair of laterally directed slides 117, 118 which define a lateral path of travel. Also, an AC reversible electric motor 120 is mounted in the base member 112 and the output of the motor is connected to a laterally extending threaded drive screw 121 which is disposed between the slides 117, 118. The output of the motor 120 is also connected to a potentiometer (not shown) for signalling the lateral position of the seat assembly 115 to the computer controller 15.

As best seen in FIG. 2, the longitudinal path of movement of the actuator is disposed perpendicular to and on one side of the lateral path of movement of the seat assembly, and the forward end of the longitudinal path of movement is disposed immediately adjacent the lateral path of movement at about its midpoint along the length of the lateral path of movement.

The seat post 114 includes a lower frame 122 which includes a pair of downwardly open C-shaped grippers 124, 125 for engaging the two slides 117, 118 respectively. Also, the lower frame 122 mounts a nut 126 which threadedly engages the drive screw 121, so that rotation of the drive motor 120 causes the post 114 to slide back and forth along the lateral path of movement defined by the slides 117, 118. The post 114 further includes a telescopic pillar 128 which is fixed to the frame 122, and which has a construction corresponding to that of the actuation pillar 49 as described above. Generally, the seat pillar 128 comprises an interior tubular member 129, an intermediate tubular member 130, and an outer tubular member 131, which telescope with respect to each other. Also, a threaded rod 132 is fixed to the frame 122 so as to coaxial with the vertical axis 133 of the seat post 114, and a sleeve 134 is threaded upon the rod 132. An AC reversible drive motor 135 is mounted in the interior tubular member to effect rotation of the sleeve 134 and thus telescopic extension and retraction of the pillar 128 in a manner corresponding to that described above with respect to the actuation pillar 49. Also, a potentiometer 136 is provided which signals the elevation of the pillar 128 to the computer controller 15.

The upper end of the interior tubular member 129 is closed, and a circular external gear 138 is coaxially fixed thereto. A shaft 139 is coaxially mounted to the gear 138, and the shaft 139 rotatably mounts a mounting plate 142, such that the mounting plate 142 is free to rotate about the vertical axis 133.

A cylindrical inner sleeve 143 is coaxially fixed to the gear 138 so as to surround the pillar 128, and the lower end of the sleeve 143 includes a surrounding collar 144, which has an angular scale printed thereon. A cylindrical outer sleeve 146 depends from the mounting plate 142 so as to encircle the inner sleeve 143. The lower edge of the outer sleeve 146 overlies the circular collar 144 and includes a pointer 147 (FIG. 20), so that the user can visually determine the angular position of the mounting plate 142 and thus the seat assembly 115.

Figure 11:
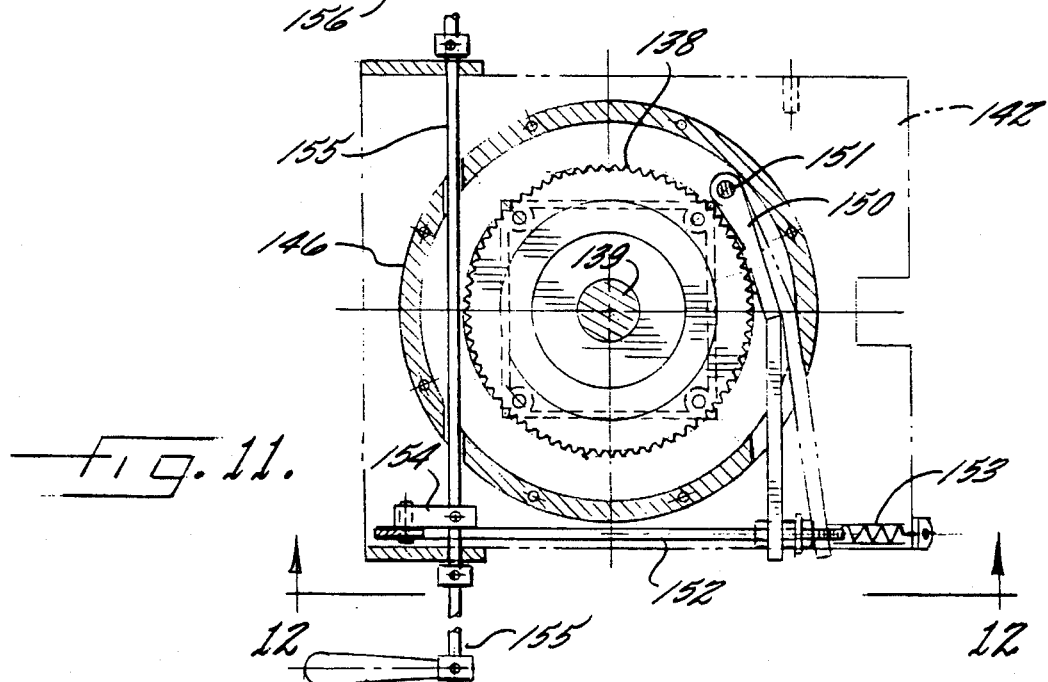
FIG. 11 is a fragmentary and sectioned top plan view taken substantially along the line 11—11 of FIG. 9.
Figure 12:
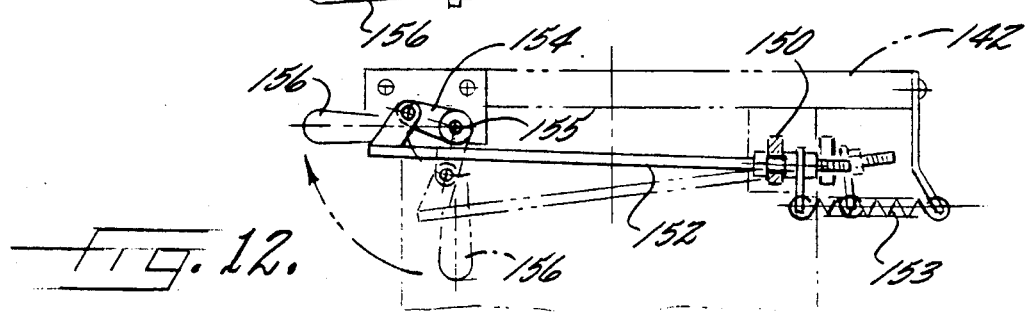
FIG. 12 is a fragmentary side elevation view taken substantially along the line 12—12 of FIG. 1.
Figure 29:
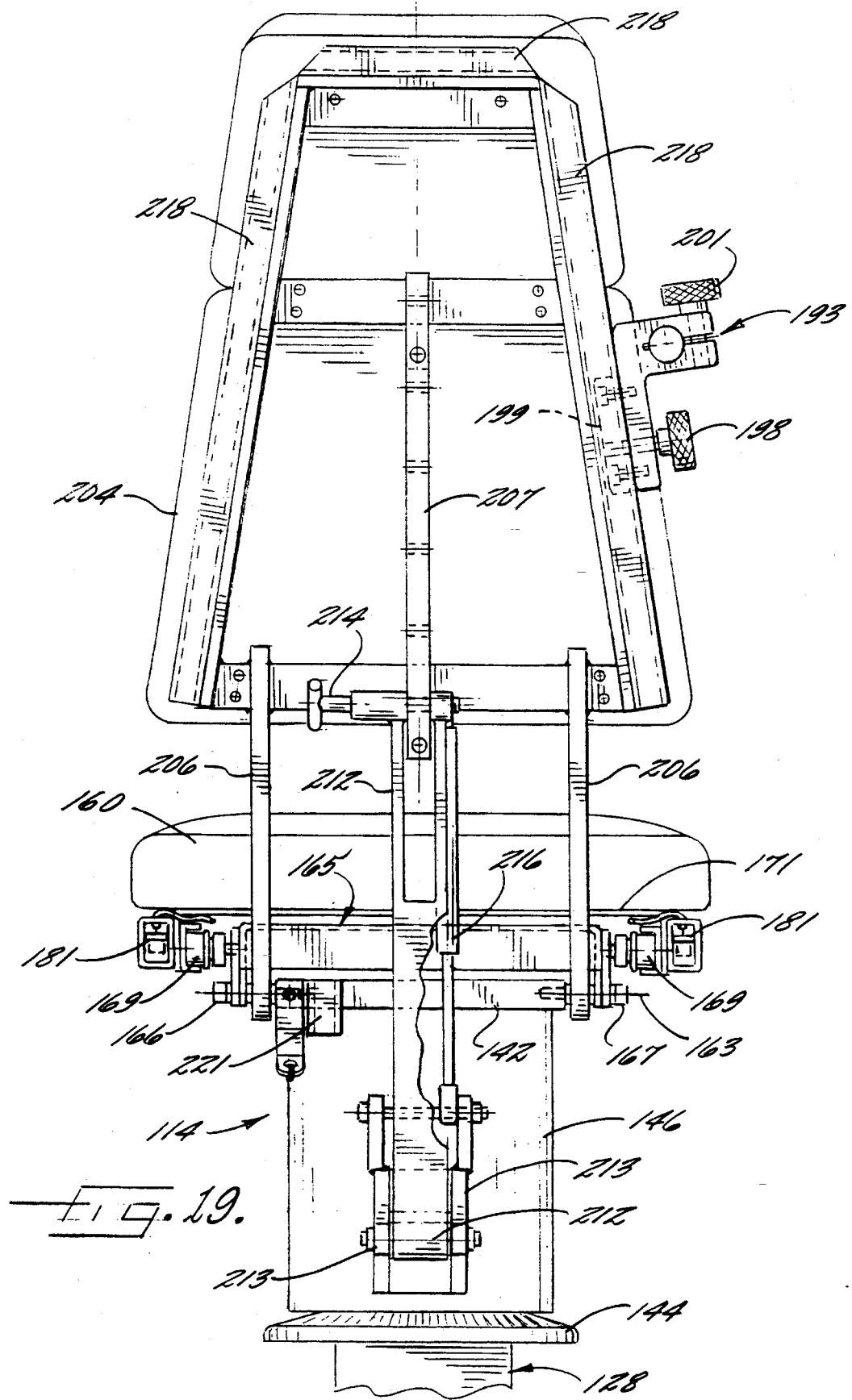

To permit the rotational position of the mounting plate to be adjusted and locked in a selected position, there is provided a locking rack 150 (FIG. 11) which is pivotally mounted to the mounting plate at 151, and which is adapted to selectively engage the circular gear. The locking rack 150 has a free end which is connected to a push-pull rod 152, which in turn is biased toward the right as seen in FIG. 11 by a spring 153, so as to withdraw the locking rack 150 from the circular gear 138 and thus permit free rotation of the mounting plate 142. To preclude such rotation, the left end of the push-pull rod 152 is connected via a toggle linkage 154 to a transverse control rod 155 which is rotatably mounted to the mounting plate 142. The control rod 155 is fixed to the upper arm of the linkage 154, and a handle 156 is mounted to each end of the rod 155 for permitting the rod to be manually rotated. Thus when the handle 156 is rotated clockwise as seen in FIG. 12, the toggle linkage 154 acts to draw the push-pull rod 152 toward the left to pivot the locking rack 150 into engagement with the circular gear 138. By pivoting the handle 156 so that the linkage 154 moves past its "dead center" position, the linkage will hold the locking rack 150 in contact with the circular gear 138, until the handle 156 is again moved counter clockwise so as to release the linkage and permit the spring to withdraw the locking rack from the circular gear.

The seat assembly 115 comprises a relatively flat and cushioned seat portion 160, which is mounted to the mounting plate 142 and which defines a front edge portion 161 and a rear edge portion 162. The means mounting the seat portion 160 to the mounting plate 142 permits selective slidable movement relative to the mounting plate along a generally horizontal direction which extends between the front and rear edge portions and between a forward position and a rearward position, note FIGS. 13 and 14, and it also permits selective pivotal movement of the front edge portion 161 relative to the rear edge portion 162 about a first horizontal axis 163 (FIG. 15) which is perpendicular to the horizontal direction, and so as to permit the front edge portion 161 to be lifted with respect to the rear edge portion 162 and thereby tilt the seat portion 160.

The mounting means which permits the above described movements of the flat seat portion 160 is best seen in FIGS. 13–15, and it includes a seat subframe 165 which is pivotally mounted to the mounting plate 142 for pivotal movement the horizontal axis 163 defined by the pins 166, 167 (FIG. 15) and which is perpendicular to the above-identified horizontal direction of seat portion movement. The opposite side edges of the seat subframe each mount two pairs of roller assemblies 169, note FIG. 13. The mounting means further includes a seat primary frame 171 which is fixed to the flat seat portion 160, and the primary frame 171 includes opposite sides which mount opposing, C-shaped channels 172 (FIG. 15) which receive the roller assemblies 169 of the seat subframe 165.

The mounting means for the seat assembly further includes a longitudinally extending slide rod 174 which is connected to forward edge of the seat primary frame 171 and slideably extends through a transverse plate 176 which is fixed to the seat subframe 165, note FIG. 14. A locking sleeve 178 of conventional design is mounted so as to coaxially surround the slide rod 174 and the sleeve 178 is fixed to the transverse plate 176 and it includes a clip 179 which releasably engages the rod. A locking sleeve and clip of this type is conventional, and is further described in U.S. Pat. Nos. 3,760,911 and 3,860,098. The clip 179 is connected to a flexible control wire 180 which leads to a release switch 181, such that upon manual closing of the switch 181 the clip 179 disengages the slide rod 174, so as to permit the seat primary frame 171 to slide forward and back with respect to the seat subframe 165 and mounting plate 142.

The mounting means for the seat assembly also includes a gas spring 184 which includes a tubular cylinder having an internal piston (not shown) which is connected to a plunger 185, and the plunger extends from the lower end of the cylinder and is pivotally attached to the outer sleeve 146 of the post 114. A cap 186 at the opposite end is pivotally connected to the seat subframe 165. A release mechanism for the gas spring 184 is provided which includes the cap 186 and a transverse control rod 187 (FIGS. 17 and 18) which extends between the sides of the seat subframe, with a handle 188 on each end. The control rod 187 mounts a lever 190, which in turn is connected to the cap 186 of the gas spring 184. The construction of the gas spring 184 is conventional, and upon rotation of the control rod 187 counter clockwise as seen in FIG. 17, the gas is released from one side of the piston to the other, causing the plunger 185 to be extended and the seat subframe 165 and seat portion 160 to be tilted upwardly. To lower the seat portion, the handle 188 is rotated counter clockwise and the seat portion is manually pushed downwardly against the force of the gas spring, and so as to cause the gas to return to the one side of the piston.

An outwardly open C-shaped car track 192 is fixed to each of the opposite sides of the seat primary frame 171, and a further car track 192 is mounted along the front edge of the seat primary frame. These car tracks are adapted to receive and slideably mount one or more car assemblies 193, note FIGS. 15 and 16, which are configured to mount the rod portion 194 of a patient engaging pad 195 in the manner best seen in FIG. 1. More particularly, each car assembly 193 has two arms 196, 197 disposed in an L-shaped configuration as seen in FIG. 16, with one arm 196 having an aperture to receive a threaded member 198 which threadedly engages a bar 199 located within the car track 192. Thus, upon tightening of the threaded member 198, the assembly may be locked in a selected position. The other arm 197 is split, with a bore extending therethrough, and a threaded member 201 is interconnected between the split sections so as to permit the rod portion 194 which is received in the bore to be releasably gripped. The rod portion and the patient engaging pad 195, may take different configurations as seen in FIG. 1.

Figure 9:
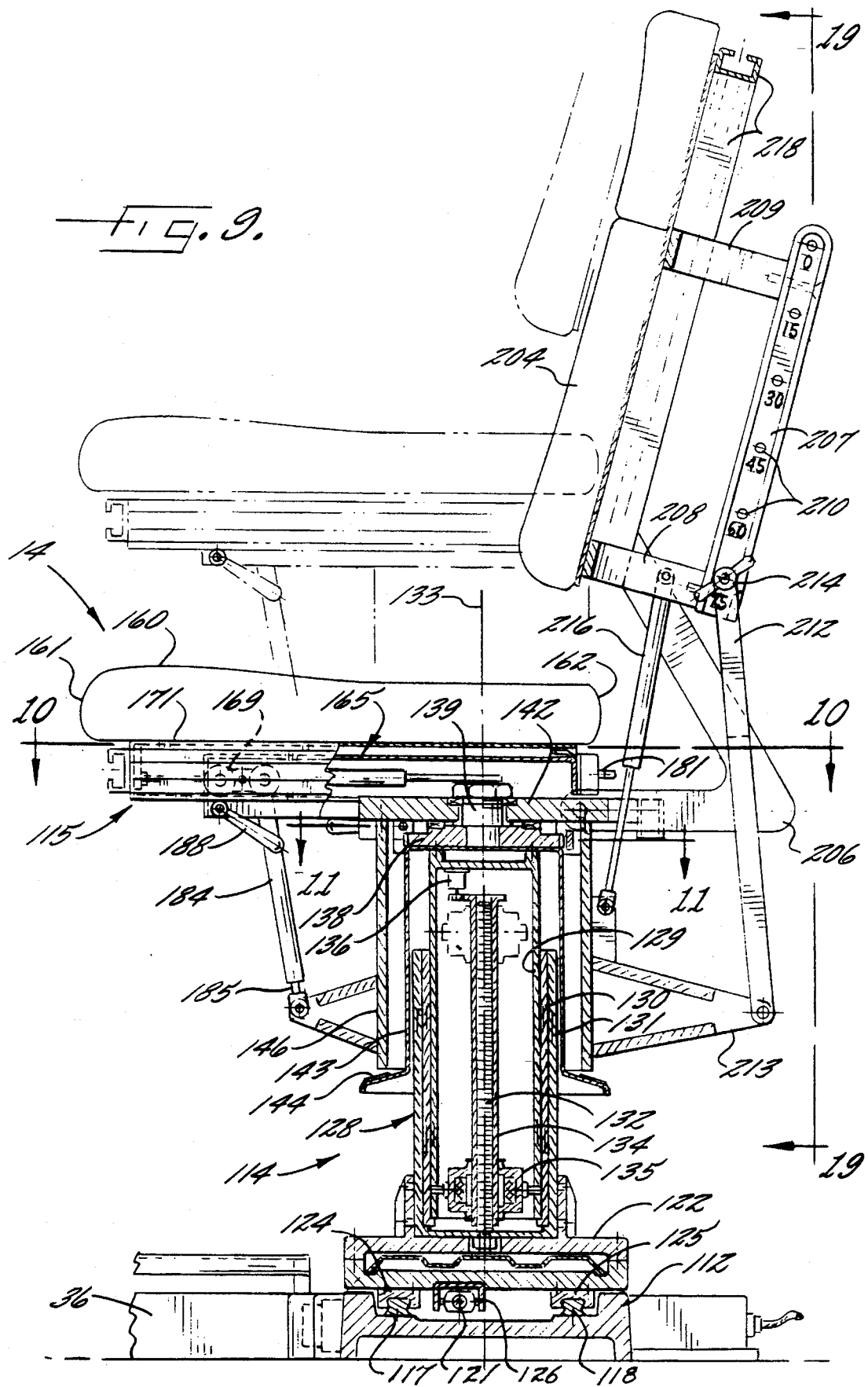
FIG. 9 is a sectioned side elevation view of the seat assembly and taken substantially along the line 9—9 of FIG. 2.

The seat assembly also comprises a back rest 204, which is mounted to the mounting plate 142 for pivotal movement about the transverse horizontal axis 163 defined by the pins 166, 167, which as noted above is perpendicular to the horizontal direction of sliding movement of the seat primary frame 171 with respect to the mounting plate 142. Thus, the back rest 204 may be pivoted between an upright position substantially perpendicular to the seat portion (FIG. 9) and a lowered position substantially co-planar with the seat portion (FIG. 20).

The mounting structure for the back rest includes a pair of L-shaped brackets 206, with the forward end of each bracket being pivotally connected to the mounting plate 142 by the pins 166, 167 for rotation about the transverse horizontal axis 163. The opposite end of each bracket 206 is fixed to the frame of the back rest 204. A position control bar 207 is mounted to the frame of the back rest by means of a pair of parallel mounting bars 208, 209, and so as to extend along the back side of the back rest. The position control bar 207 includes a plurality of spaced apart apertures 210. A linkage 212 is also provided which has one end pivotally connected to a bracket 213 which is fixed to the outer sleeve 146, and the opposite end of the linkage 212 mounts a pin 214 for releasable connection in a selected one of the apertures 210 of the control bar 207. By this arrangement, the back rest 204 may be tilted rearwardly and locked in about 15° increments between the upright and lowered positions. Also, a gas spring 216 is provided which is connected between a bracket on the outer sleeve 146 and one of the mounting bars 208 for the control bar 207. The gas spring 216 acts to bias the back rest toward its upright position, so as to facilitate the lifting thereof from its lowered position and also preclude rapid falling thereof in the opposite direction.

An outwardly open C-shaped car track 218 is fixed to each side of the frame of the back rest, and the car tracks 218 are adapted to receive one or more car assemblies 193 as described above and which are adapted to mount patient engaging pads to the back rest.

Figure 10:
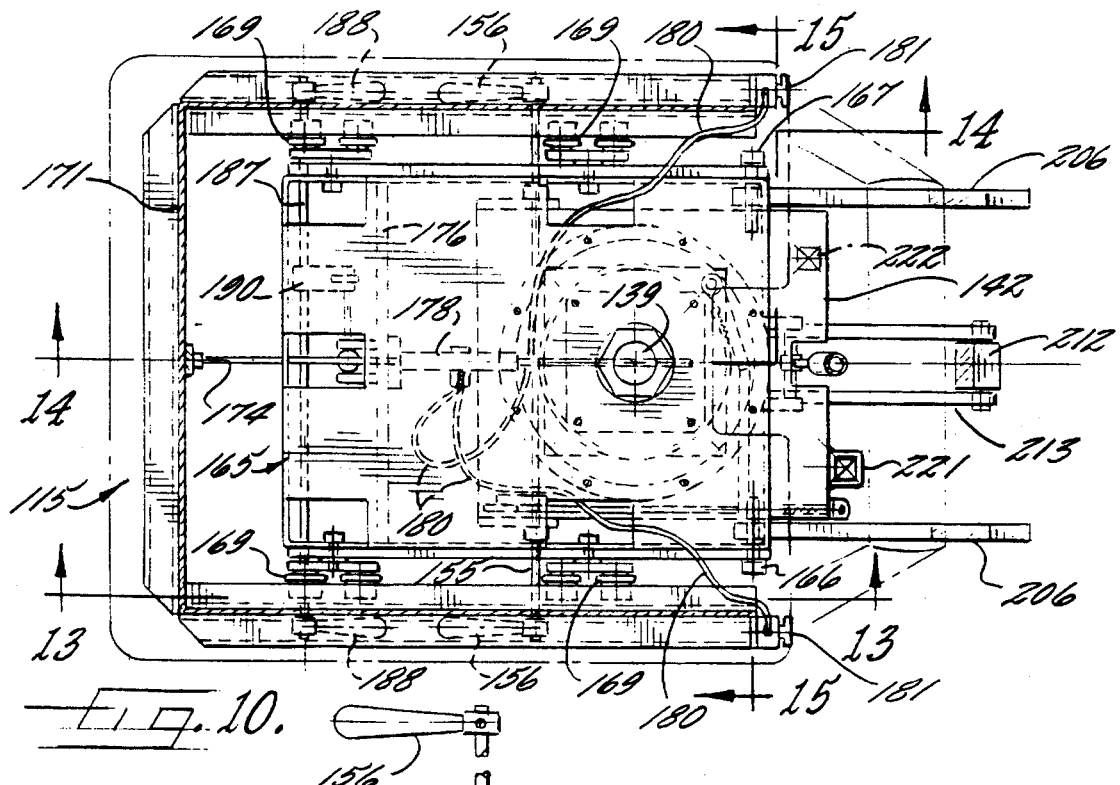
FIG. 10 is a sectioned top plan view of the seat assembly taken substantially along the line 10—10 of FIG. 9.

With the seat portion 160 in its forward position and with the back rest 204 in its fully lowered position as seen in FIG. 20, it will be noted that there is an open gap of significant length in the mid-portion of the seat assembly. To close this gap, and thus provide increased comfort to a patient lying upon the assembly, there is provided an intermediate pad 220 which can be removably mounted in the gap. For this purpose, the mounting plate 142 mounts a vertically open rectangular sleeve 221 at its rear edge, and an abutment 222 (FIG. 10) is fixed to the rear edge at a location laterally spaced from the sleeve 221. The intermediate pad 220 includes a depending rectangular post 224 extending from its bottom side which is adapted to be received in the sleeve 221, and a second post 225 which is adapted to engage the abutment 222. Thus, as will be apparent from FIG. 20, the intermediate pad 220 may be vertically dropped into its operative position, and later lifted therefrom.

As noted above, and as best seen in FIG. 20, the rotational position of the seat assembly 115 with respect to the vertical axis 133 may be visually determined from the pointer 147 on the outer sleeve 146 and the scale on the collar 144. The forward and rearward positions of the seat portion 160 may be determined from the scale 227 on the mounting plate and the associated pointer 228 mounted on the seat primary frame, and the angular tilted position of the seat portion may be determined 229 from the scale which is fixed to the seat subframe 165 and the pointer 230 which is fixed to the mounting plate 142. Thus, the various positions of these components for a particular exercising routine can be readily observed and recorded, so as to facilitate the later set-up of the apparatus when the same exercising routine is to be repeated for the same patient.

Patient Positioning System

The present invention incorporates a novel patient positioning system wherein the elevational and longitudinal or lateral positions of the seat assembly and actuator may be readily adjusted. This patient positioning system may be manually operated, or it may be automatically operated with the assistance of the computer controller 15 as fully described in the copending and commonly owned application entitled "Patient Positioning System for Computer Controlled Exercising Machine", and filed concurrently herewith.

As seen in FIG. 3, the patient positioning system includes a seat switch 231 and an actuator (or head) switch 232, which are preferably mounted on a panel adjacent the keyboard 18. The seat switch 231 has four contacts, namely, an "up" contact 234 for operating the motor 135 to lift the seat assembly, a "down" contact 235 for operating the motor 135 to lower the seat assembly, a "left" contact 236 for operating the motor 120 to laterally move the seat assembly toward the left, and a "right" contact 237 for operating the motor 120 to laterally move the seat assembly toward the right. The actuator switch 232 also has four contacts, namely, an "up" contact 238 for operating the motor 55 to lift the actuator, a "down" contact 239 for operating the motor 55 to lower the actuator, a "forward" contact 240 for operating the motor 40 to move the actuator in the forward direction, and a "back" contact 241 for operating the motor 40 to move the actuator in the rearward direction.

A light may be positioned on the panel in association with each of the four contacts of each switch, as schematically illustrated in FIG. 3, so as to permit the computer controller 15 to prompt the operator to properly actuate the two switches to facilitate the positioning of the seat assembly and actuator in accordance with information which has been previously stored in the memory of the computer relating to the particular exercise and the particular patient, and as fully described in the above noted copending application. Once the positions are established for the particular exercise and the particular patient, the operator then manually adjusts the rotational positions of the first and second housing members, the rotational position of the seat assembly, the forward and back position of the seat portion, the tilting of the seat portion, and the position of the back rest, to complete the set-up of the apparatus.

Description of Representative Positions

FIGS. 22–25 are presented for the purpose of illustrating the flexibility of the positioning of the apparatus of the present invention, which in turn permits a wide variety of exercising modes. In this regard, and as noted above, it is important that the apparatus have sufficient flexibility in its positioning capability to permit the rotational axis 30 of the output shaft 29 of the rotary actuator 26 to be aligned with the joint which is being exercised or evaluated in a particular mode of operation.

Figure 22:
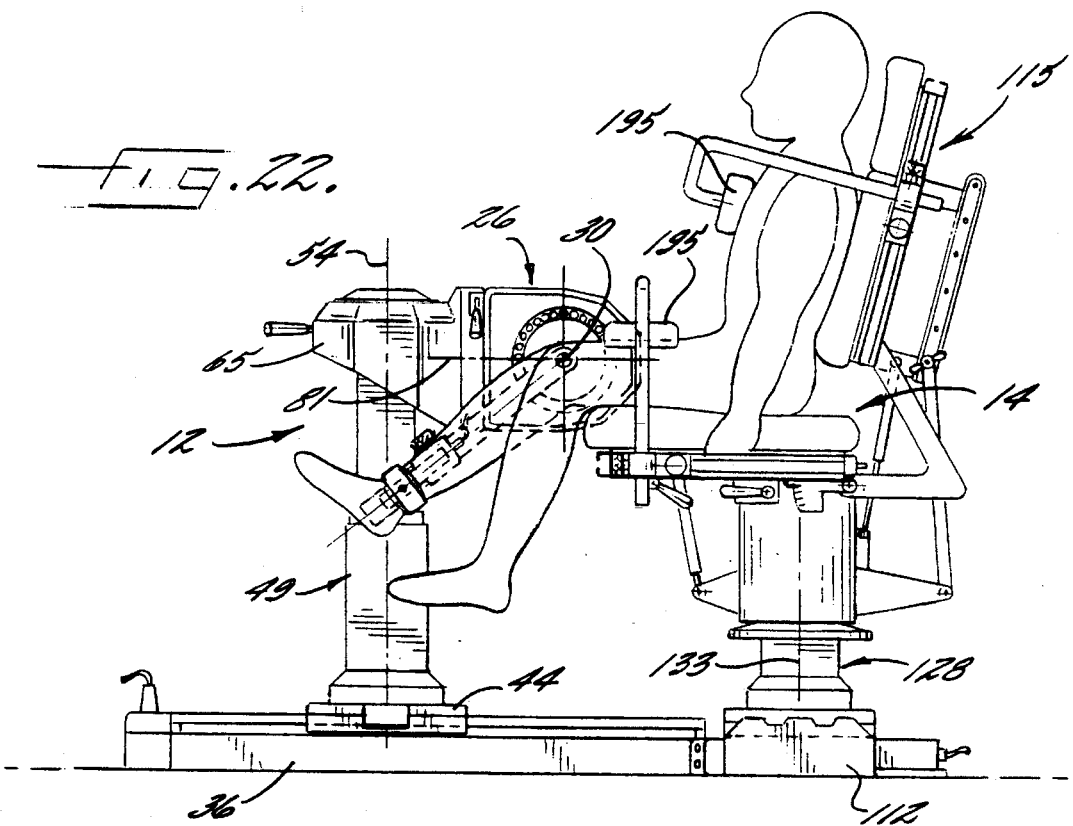
FIGS. 22 and 23 are side and front elevation views respectively of the apparatus of the present invention and positioned for performing an exercising routine for the right leg of a patient seated on the seat assembly.
Figure 23:
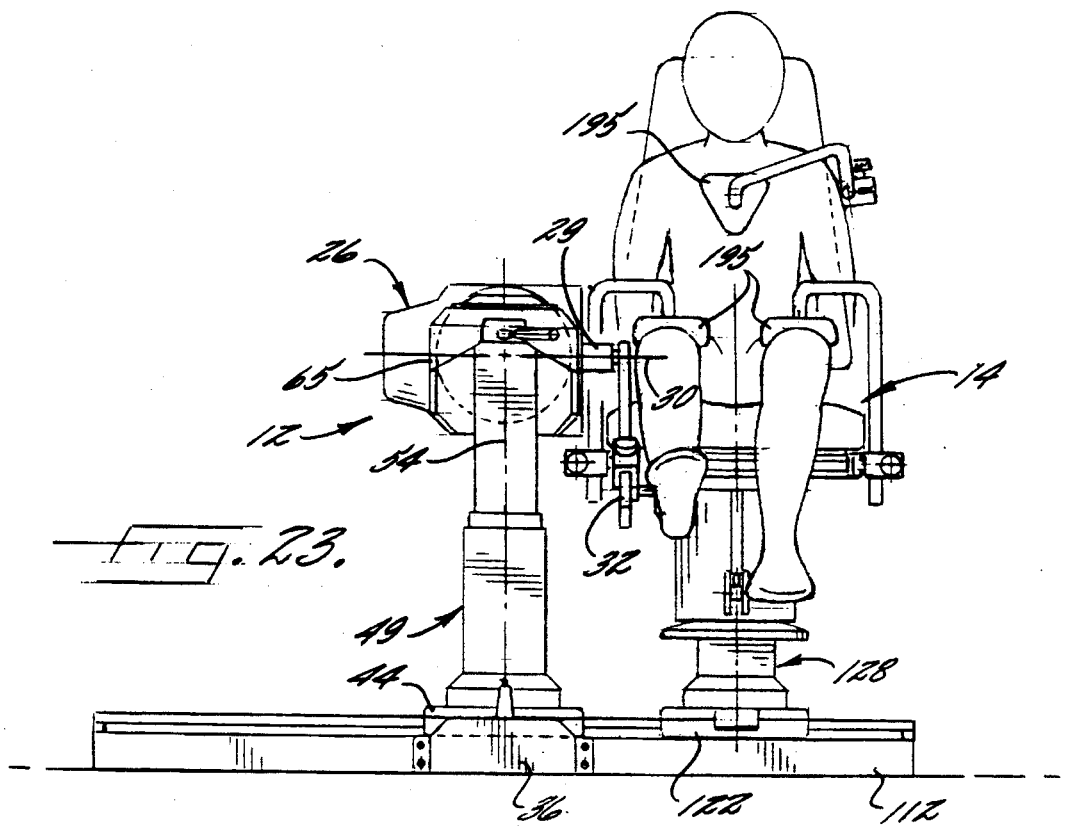
Figure 24:
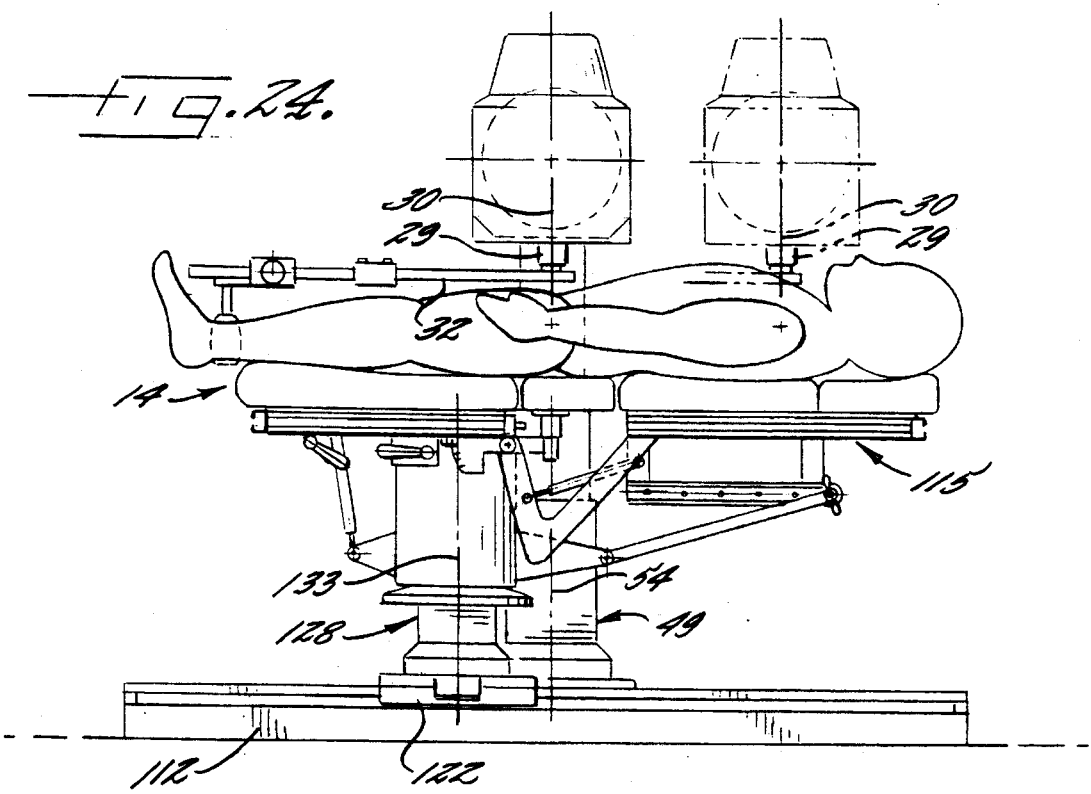
FIG. 24 is a side elevation view of the apparatus configured for performing a gravity eliminated exercise for the right hip of a patient, and further illustrating the position of the actuator in dashed lines when set-up to perform a gravity eliminated exercise for the right shoulder of a patient.
Figure 25:
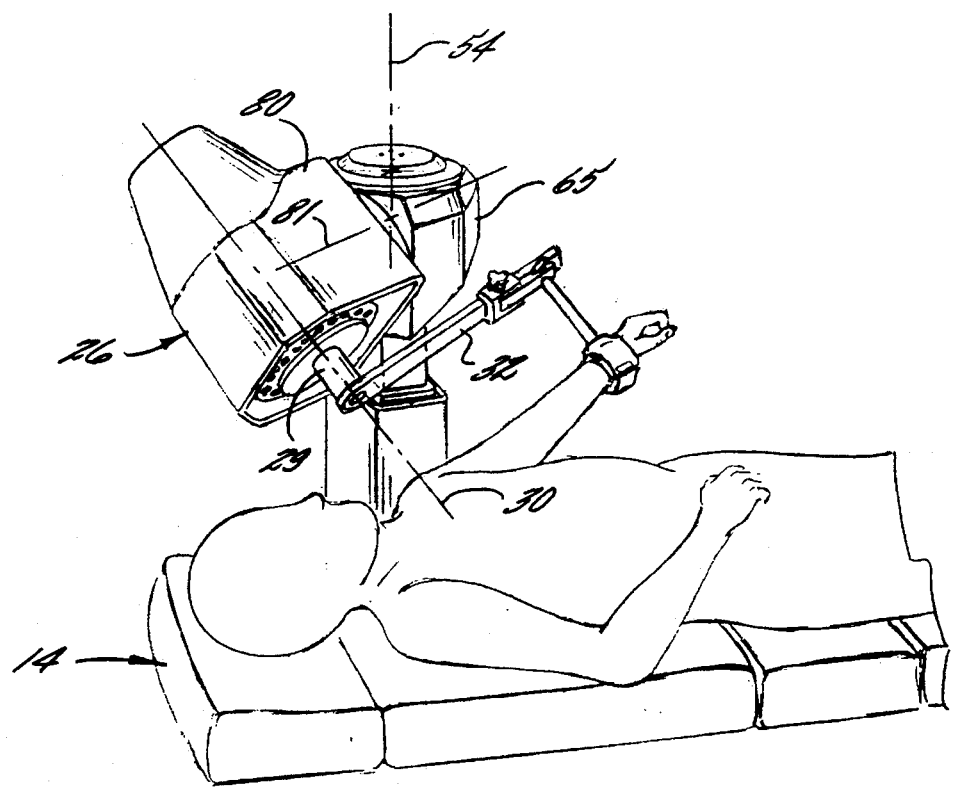
FIG. 25 is a perspective view illustrating the apparatus configured for performing an exercising routine on the left shoulder of a patient.

FIGS. 22 and 23 illustrate the apparatus configured so as to subject the right knee of the patient to flexion - extension, and with the rotational axis 30 of the rotary actuator 26 being aligned horizontally so as to pass through the joint of the right knee. FIG. 24 illustrates a gravity eliminated exercise, wherein the right hip of a patient lying upon the seat assembly 115 may be subjected to flexion extension in a horizontal direction, and wherein the rotational 30 axis is directed vertically through the hip joint. FIG. 24 also illustrates, in dashed lines, the position of the actuator 26 for performing a gravity eliminated exercise on the right shoulder of the patient. FIG. 25 illustrates a PNF exercise, wherein the patient lies on his or her back, and the patient's arm moves between a down position at the side of the patient to an up and across position on the opposite side. As illustrated, the actuator 26 is oriented so that the rotational axis 30 is aligned with the left shoulder joint of the patient.

In the drawings and specification, there has been set forth a preferred embodiment of the invention, and although specific terms are employed, they are used in a generic and descriptive sense only and not for purposes of limitation.

That which is claimed is:

1. A muscle exercise and rehabilitation apparatus comprising a rotary actuator comprising an output shaft defining a rotational axis, an arm connected to said output shaft and extending radially therefrom and so as to be adapted for engagement by a patient, and drive means for selectively rotating said shaft in either direction about said rotational axis, and actuator mounting means comprising a vertically disposed post which defines a vertical axis, a first housing member, means mounting said first housing member to said post for rotation about said vertical axis, a second housing member, means mounting said second housing member to said first housing member for rotation about a horizontal axis which is fixed with respect to said first housing member, and means mounting said rotary actuator to said second housing member with said rotational axis of said output shaft being disposed in a vertical plane which is perpendicular to said horizontal axis and offset from said vertical axis of said post a distance sufficient such that said rotary actuator can be rotated through a rotational range of movement about said horizontal axis so as to permit the rotational axis of said output shaft selectively to be disposed vertically in either direction and horizontally in either direction.

2. The apparatus as defined in claim 1 wherein said horizontal axis perpendicularly intersects said vertical axis of said post and said rotational axis of said output shaft perpendicularly intersects said horizontal axis.

3. The apparatus as defined in claim 1 wherein said actuator mounting means further comprises first abutment means mounted to said post and said first housing member for precluding rotational movement of said first housing member about said vertical axis beyond about 360 degrees.

4. The apparatus as defined in claim 3 wherein said actuator mounting means further comprises second abutment means mounted to said first housing member and said second housing member for precluding rotational movement of said second housing member about said horizontal axis beyond about 360 degrees.

5. The apparatus as defined in claim 4 wherein said actuator mounting means further comprises a first circular gear mounted to one of said post and first housing member and so as to be coaxial with said vertical axis, a first rack gear mounted to the other of said post and first housing member, and first control lever means for selectively moving said first rack gear radially into engagement with said first circular gear and so as to preclude relative rotation between said post and said first housing member.

6. The apparatus as defined in claim 5 wherein said actuator mounting means further comprises a second circular gear mounted to one of said first housing member and said second housing member and so as to be coaxial with said horizontal axis, a second rack gear mounted to the other of said first housing member and said second housing member, and second control lever means for selectively moving said second rack gear radially into engagement with said second circular gear and so as to preclude relative rotation between said first housing member and said second housing member.

7. The apparatus as defined in claim 1 wherein said actuator mounting means further comprises a base member supporting said post, and means for selectively effecting collective vertical movement of said first and second housing members and said actuator with respect to said base member.

8. The apparatus as defined in claim 7 wherein said actuator mounting means further comprises means mounting said post to said base member so as to permit horizontal movement of said post in either direction along a longitudinal path of movement, and drive means for effecting such horizontal movement in either direction.

9. The apparatus as defined in claim 8 further comprising a seat for supporting a patient thereon, and means mounting said seat adjacent said longitudinal path of movement so that a patient positioned on said seat can engage said arm of said actuator.

10. The apparatus as defined in claim 9 wherein said means mounting said seat comprises a seat base member, and means mounting said seat to said seat base member for selective movement in either direction along a linear, laterally directed path of movement, and with said longitudinal path of movement being disposed perpendicular to and on one side of said lateral path of movement and having one end which is disposed immediately adjacent said lateral path of movement at a medial location along the length of said lateral path of movement.

11. The apparatus as defined in claim 1 wherein said offset between said rotational axis of said output shaft and said vertical axis of said post is at least 15 inches.

12. A muscle exercise and rehabilitation apparatus comprising a seat for supporting a patient thereon, seat mounting means comprising a seat base member, a vertical first post slideably mounted to said seat base member for selective movement in either direction along a linear, laterally directed path of movement, with said first post defining a vertical seat axis, and means mounting said seat to said first post for selective rotation about said vertical seat axis, a rotary actuator, and comprising an output shaft defining a rotational axis, an arm connected to said output shaft and extending radially therefrom, and drive means for selectively rotating said shaft in either direction about said rotational axis, actuator mounting means mounting said actuator adjacent said seat so that a patient supported on said seat can engage said arm of said actuator, and comprising an actuator base member, a vertical second post slideably mounted to said actuator base member for selective movement in either direction along a linear, longitudinally directed path of movement, with said second post defining a vertical actuator axis, and means mounting said actuator to said second post for rotation about said vertical actuator axis, and with said longitudinal path of movement being disposed perpendicular to and on one side of said lateral path of movement and having one end which is disposed immediately adjacent said lateral path of movement at a medial location along the length of said lateral path of movement, said actuator mounting means comprising a first housing member, means mounting said first housing member to said second post for rotation about said vertical actuator axis, a second housing member, means mounting said second housing member to said first housing member for rotation about a horizontal axis which is fixed with respect to said first housing member, and means mounting said rotary actuator to said second housing member with said rotational axis of said output shaft being disposed in a vertical plane which is perpendicular to said horizontal axis and offset from said vertical actuator axis of said second post a distance sufficient such that said rotary actuator can be rotated through about 360 degrees about said horizontal axis so as to permit the rotational axis of said output shaft selectively to be disposed vertically in either direction and horizontally in either direction.

13. The apparatus as defined in claim 12 wherein said offset between said rotational axis of said output shaft and said vertical actuator axis of said second post is at least about one half the length of said longitudinal path of movement.

14. The apparatus as defined in claim 12 wherein said offset between said vertical plane of said rotational axis of said output shaft and said vertical actuator axis of said second post is at least 15 inches.

15. The apparatus as defined in claim 12 wherein said seat mounting means further comprises means for permitting selective vertical movement of said seat.

16. The apparatus as defined in claim 15 wherein said actuator mounting means further comprises means for permitting selective vertical movement of said actuator.

17. The apparatus as defined in claim 16 wherein said seat includes a generally horizontal bottom support member, and a backrest, and means interconnecting said backrest to said bottom support member so as to permit pivotal movement of said backrest about a horizontal axis and between an upright position forming a chair-like configuration with said bottom support member, and a horizontal position forming a generally flat bunk-like configuration with said bottom support member.

18. The apparatus as defined in claim 17 wherein said means interconnecting said backrest to said bottom support member comprises means permitting relative horizontal movement between said bottom support member and said backrest so as to permit the same to be separated when in said bunk-like configuration and so as to form a space therebetween, and said apparatus further comprises a support pad sized to be received in said space, and means releasably mounting said pad in said space so as to be horizontally aligned between said bottom support member and said backrest.

19. The apparatus as defined in claim 12 wherein said horizontal axis perpendicularly intersects said vertical actuator axis of said second post, and wherein said rotational axis of said output shaft perpendicularly intersects said horizontal axis.

* * * * *